(12) United States Patent
Koshti et al.

(10) Patent No.: US 12,109,283 B2
(45) Date of Patent: Oct. 8, 2024

(54) SAFE AND ECOFRIENDLY PERSISTENT SANITIZING GEL FOR TOPICAL APPLICATION

(71) Applicant: GALAXY SURFACTANTS LTD., Mumbai (IN)

(72) Inventors: Nirmal Koshti, Piscataway, NJ (US); Bhagyesh Jagannath Sawant, Kalyan (IN); Kishor Pundalik Bari, Pavel (IN); Bilal Momin, Bhiwandi (IN); Sushant Khandekar, Kalyan (IN); Sukanya Talukdar, Thane (IN); Parag Narendra Savla, Bhiwandi (IN); Ananda Shamrao Hodage, Dombivali (IN); Pooja Vaidya, Nagpur (IN)

(73) Assignee: GALAXY SURFACTANTS LTD.

( * ) Notice: Subject to any disclaimer, the term of this patent is extended or adjusted under 35 U.S.C. 154(b) by 214 days.

(21) Appl. No.: 17/444,896

(22) Filed: Aug. 11, 2021

(65) Prior Publication Data

US 2022/0226209 A1   Jul. 21, 2022

(30) Foreign Application Priority Data

Jan. 20, 2021   (IN) .............................. 202121002782

(51) Int. Cl.
| | | |
|---|---|---|
| *A61Q 17/00* | (2006.01) | |
| *A61K 8/04* | (2006.01) | |
| *A61K 8/19* | (2006.01) | |
| *A61K 8/92* | (2006.01) | |

(52) U.S. Cl.
CPC ................ *A61K 8/19* (2013.01); *A61K 8/042* (2013.01); *A61K 8/922* (2013.01); *A61Q 17/005* (2013.01); *A61K 2800/413* (2013.01); *A61K 2800/48* (2013.01)

(58) Field of Classification Search
CPC ...... A61Q 17/005; A61Q 19/00; A61K 45/06; A61K 9/0014; A61K 8/34; A61K 2800/10; A61K 33/38; A61K 8/042; A61K 47/10; A61K 2800/413; A61P 31/04
See application file for complete search history.

(56) References Cited

U.S. PATENT DOCUMENTS

| | | | | |
|---|---|---|---|---|
| 2010/0203088 A1* | 8/2010 | Sanjeev | .................. | A61P 17/02 977/773 |
| 2011/0038965 A1* | 2/2011 | McKay | .................. | A61K 45/06 514/25 |
| 2013/0280312 A1* | 10/2013 | De Szalay | ............. | A61K 8/553 424/408 |
| 2017/0087073 A1* | 3/2017 | Gunn | ..................... | A61K 8/891 |
| 2018/0133124 A1 | 5/2018 | Bechert et al. | | |
| 2019/0029970 A1* | 1/2019 | Lee | ......................... | A61K 31/12 |
| 2022/0142902 A1* | 5/2022 | Tian | ..................... | A61K 8/4946 |

FOREIGN PATENT DOCUMENTS

| | | | | |
|---|---|---|---|---|
| AU | 322839 S | 12/2008 | | |
| CN | 101766552 A | 7/2010 | | |
| CN | 107440925 A | 12/2017 | | |
| CN | 110613620 A | 12/2019 | | |
| CN | 111514093 A | 8/2020 | | |
| DE | 60022344 T2 | 7/2006 | | |
| EP | 3177142 A1 | 6/2017 | | |
| WO | WO-2012168126 A2 * | 12/2012 | ............... | A61K 8/44 |

OTHER PUBLICATIONS

Lee et al. Tung Oil Based Production of High 3-Hydroxyhexanoate-Containing Terpolymer Poly(3-Hydroxybutyrateco-3-Hydroxyvalerate-co-3Hydroxyhexanoate) Using Engineered Ralstonia eutropha. Polymers 2021,13,1084. https:// doi.org/10.3390/polym13071084. (Year: 2021).*
Deshmukh, et al., Silver nanoparticles as an effective disinfectant: A review, Materials Science & Engineering, 2019, 954-965.
Fouad, et al., Influence of Handprint Culture Training on Compliance of Healthcare Workers with Hand Hygiene, Interdisciplinary Perspectives on Infectious Diseases, 2018, 6 pages.
Jain, et al., Silver Nanoparticles in Therapeutics: Development of an Antimicrobial Gel Formulation for Topical Use, Molecular Pharmaceutics, 2009, 6:5:1388-1401.
Lewis, et al., Dietary α-Eleostearic Acid Ameliorates Experimental Inflammatory Bowel Disease in Mice by Activating Peroxisome Proliferator-Activated Receptor-γ, Plos One, 2011, 14 pages.
Martha A. Belury, Inhibition of Carcinogenesis by Conjugated Linoleic Acid: Potential Mechanisms of Action, American Society for Nutritional Sciences, 2002, 2995-2998.
Moon, et al., Alpha-eleostearic acid suppresses proliferation of MCF-7 breast cancer cells via activation of PPARγand inhibition of ERK 1/2, Cancer Sci, 2010, 101:2:396-402.
Paul, et al., A novel nanoformulation of α-eleostearic acid restores molecular pathogenesis of hypersensitivity, Nanomedicine (Lond.), 2019, 24 pages.
Reilman, et al., Towards an antimicrobial 'microglove', Scientific Reports, 2015, 11 pages.

* cited by examiner

*Primary Examiner* — Tracy Liu
(74) *Attorney, Agent, or Firm* — Blank Rome LLP

(57) ABSTRACT

The invention discloses persistent antimicrobial protection of hands and/or surfaces of different objects using the hydro-alcoholic gel composition of the present invention. In particular, the invention provides water-resistant sanitizing hydro-alcoholic gel compositions based on ethyl alcohol, silver nanoparticles and fatty acids of Tung seed oil (*Aleurites fordii*). More particularly, it discloses the compositions that keep the surface sanitized well beyond the instant sanitization provided by volatile ethyl alcohol. The compositions of the present invention have 'natural origin' index of minimum 99% as per ISO 16128-2.

10 Claims, 7 Drawing Sheets

SAFE AND ECOFRIENDLY PERSISTENT SANITIZING GEL FOR TOPICAL APPLICATION

FIELD OF THE INVENTION

This application claims the benefit of India Application No. 202121002782, filed Jan. 20, 2021, the entire contents of which are incorporated herein by reference.

FIELD OF THE INVENTION

The present invention relates to a sanitizing topical hydro-alcoholic gel composition based on ethyl alcohol, silver nanoparticles (AgNPs) and fatty acids derived from Tung seed oil (*Aleurites fordii*) for topical application. The sanitizing hydro-alcoholic gel composition of the present invention keeps the surface in sanitized state well beyond the instant sanitization provided by volatile ethyl alcohol. The composition of the present invention has 'natural origin' index of minimum 99% as per ISO 16128-2.

BACKGROUND AND PRIOR ART

Hydro-Alcoholic Gel Hand Sanitizers:

Hydro-alcoholic gels for instant sanitization of hands have been around for a while and people have been using it during travel and while visiting public places. However, during COVID-19 pandemic period (2020), this form of personal sanitization application acquired a special importance in our daily life. It sanitizes our hands instantly and efficiently without depending on the availability of water and soap or a surfactant. The entire world is using alcohol based hand sanitizers that typically employ 60% to 70% of ethyl alcohol or isopropanol or the mixtures thereof. The gel matrix of these hydro-alcoholic compositions is obtained or produced using acrylate polymers and an organic or inorganic base.

These types of acrylate gels with alcohol are good for killing the germs instantly. However, the surface of hands is repeatedly vulnerable to fresh contamination as soon as volatile alcohol evaporates. Such condition also leads to frequent use of hand sanitizers which in turn results into significant load of acrylate polymers to the ecosystem. The volatile alcohols are good antimicrobials but its repeated use by people leads to significant dryness of the skin because it practically dissolves and strips off the constituent members of skin's upper layer (stratum corneum), namely, lipids, protein and natural moisturizing factor (NMF).

To prolong the time of 'sanitized state' after the evaporation of alcohol, formulators have used additional antimicrobials that would remain on the skin and continue to protect hands (or other surfaces) from getting contaminated during the normal activity.

CN101766552 (2011) discloses disposable lower alcohol based hand sanitizing gel compositions containing ethyl alcohol/isopropanol, ionic silver (silver nitrate), chlorhexidine gluconate/acetate in tertiary amine neutralized poly acrylate (carbomer) matrix. The objective of this invention is to create long lasting 'sanitized' effect after the 'instant' sanitization by lower alcohols is affected. For this reason, chlorhexidine salts have been used in the composition described along with 'ionic' silver at ppm level. However, though chlorhexidine acetate or gluconate is a good antimicrobial, it does get deactivated by anionic polymer matrix. (Chlorhexidine is cationic in nature. It is a bis-biguanidine type of cationic molecule at physiological pH. For the same reason, Chlorhexidine doesn't meet current European specifications for hand disinfectant (water-surfactant based). Under the test conditions of European Standard EN 1499, no significant difference in the efficacy was found between 4% solution of chlorhexidine digluconate and soap). Also, its ecotoxic nature is serious cause of concern. US FDA limits its usage to six months continuously for mouthwash application. Finally, chlorhexidine is a chlorinated molecule like Triclosan which was also very popular with hand washes till the recent time. However, wanton use of Triclosan resulted in impacting environment adversely and now it has been banned and phased out by all responsible producers of hand washes (like Unilever, Johnson and Johnson, Procter and Gamble etc).

Silver nitrate (silver is in the ionic form) used in ppm level in these compositions (CN 107440925A, CN 110613620A, CN111514093A) can also get deactivated by the ubiquitous chloride ions (present in water as well as body fluids and secretions) to form insoluble silver chloride. Long term instability (EP 3177142(2018)) and reactive nature of silver ion ($Ag^+$) is well documented (*Molecular Pharmaceutics* Vol. 6, NO. 5, 1388-1401, 2009).

Typically, alcohol based disposable sanitizing hydro-alcoholic gels are made with cross linked polyacrylic acids (carbomers) neutralized by alkaline earth metal bases or organic tertiary amines Such synthetic acrylic polymer based sanitizing gels are being used more frequently (during and post pandemic era). This frequent use will pose a big challenge to the environment. Also, their strong anionic nature is not compatible with strong cationic type of antimicrobials like benzalkonium chloride or benzethonium chloride. Excessive usage of strong ecotoxic quaternary ammonium type of molecules will have serious consequences (For example, chlorhexidine is eco-toxic). Other toxic halogenated antimicrobials are not suitable to be left on the human skin (for the intended long lasting antimicrobial effect) after the evaporation of alcohol post application.

In view of aforesaid limitations (toxicity, incompatibility, biodegradability, complexity of organic synthesis using hazardous reagents) of traditional work-horse antimicrobials, colloidal silver nanoparticles (AgNPs) is a good solution to the problem of persistent hand sanitizing via alcohol based disposable hydrogel. AgNPs are expected to exhibit persistent antimicrobial protection after the alcohol is evaporated.

One such product with persistent effect is available from Nano Japan (haps://www.zalora.sg/nano-japan-nano-hand-sanitizer-with-nano-silver-bundle-of-3-with-1-x-free-1464626.html). However, this product contains synthetic polymer 'polyethylene' (polymeric petrochemical ethylene) in addition to other petrochemical based compounds like phenoxy ethanol (made from phenol and ethylene oxide) and triethanol amine (based on ethylene oxide).

Thus, chlorinated molecules (Triclosan, Triclocarban), cationic molecules (Chlorhexidine, Benzalkonium chloride, Benzethonium chloride) as well ionic silver (Ag salts) have their serious limitations in terms of toxicity, complex multistep synthesis involving hazardous chemicals and long term stability.

In today's global pandemic, the mankind needs 'instant and total' protection for their hands against bacteria and virus. This need is met by the hydro-alcoholic gels (ethyl alcohol and isopropanol) that are topically applied. During the period of global pandemic, these gels are being used with alarmingly high frequency for 'instant and complete' sanitization of hands and/or other surfaces. The biggest concern is that, though they are very effective in providing the instant sanitization, they fail to provide the 'sanitized state' for a longer time. After alcohol is evaporated, hands and surfaces are again completely vulnerable to fresh colonization of air borne bacteria and viruses. Thus, to keep hands sanitized for a longer period it is possible only by the frequent application of topical sanitizers. Frequent use of these hand sanitizers dries the skin due to solvolytic action of alcohol on the lipids and proteins of upper layers of skin. Also, due to the frequent use of the sanitizer the harsh ingredients ultimately go into the environment which produces adverse effect on the ecosystem. Hence, it is important that not only the antimicrobial used in the hand sanitizer are 'ecofriendly' but it is equally important that all other ingredients of the formulation are 'green' and environment friendly. It is also important to have formulation that continues to protect and keeps the hands germ-free for a long time, thereby reducing the frequency of application. Lesser frequency of sanitizer application means fewer loads of synthetic chemicals on the planet and on its already stressed eco-system.

Hence, to prolong the 'sanitized state', achieved by the application of alcohol containing sanitizer, there is a need for another 'safe' antimicrobial in the formulation which without being harsh can continue to protect the skin after alcohol gets evaporated for a substantial length of time without getting easily removed from hands.

Therefore, there remains a need in the art to provide an efficacious 'instant' and 'persistent' hand-sanitizer formulation that would be effective for a long time after it is applied and is completely safe to humans as well as benign to the environment. This means all the ingredients need to be biodegradable and need to be derived from 'renewable' sources and deliver the performance in terms of both 'instant' and 'persistent' sanitization.

Objectives of the Invention

1) To create a user-friendly 'instant and persistent' hand sanitizer with safe and ecofriendly antimicrobial that would provide a long lasting sanitization in order to obviate the need for frequent application of 'no-rinse' sanitizers.
2) Yet another objective of this invention is to ensure the persistent antimicrobial protection to hands by an invisible glove that will not be worn off or washed off easily by water or by friction that palms of human hands experience during normal human activity.
3) Yet another objective of the present invention is to provide the long lasting or persistent anti-microbial cover that would last for at least four hours or more and thereby the 'sanitized' status of hands is maintained for prolong period.
4) Another objective of the present invention is to create 'no rinse' hand sanitizer composition with minimum 99% of 'natural origin' content as per the definition of ISO 16128-2.

SUMMARY OF THE INVENTION

The present invention provides safe and ecofriendly sanitizing topical hydro-alcoholic gel composition for topical application with instant and persistent antimicrobial activity comprising of,
a) 60-70% by weight of ethyl alcohol;
b) 5 to 100 ppm by weight of silver nanoparticles;
c) 0.2 to 5% by weight of fatty acids derived from Tung seed oil;
d) 0.2 to 2% by weight of carbohydrate based gelling agents;
e) optionally, 1 to 5% skin benefiting agents; and
f) demineralized water to make up 100% w/w.

The hydro-alcoholic gel composition of the present invention is useful for 'instant and persistent' sanitization of hands or other surfaces wherever these are applied. The composition of the present invention reduces the frequency of application and hence avoids the adverse impact on the environment as well as on skin without compromising on efficacy. The compositions of the present invention are safe to use and eco-friendly.

In an aspect, the hydro-alcoholic gel composition of the present invention provides long lasting or persistent antimicrobial cover that would last for at least four hours or more and thereby the 'sanitized' state of hands is maintained for prolong period.

The above described features and the advantages of the present disclosures will be appreciated and understood by those skilled in the art from the 'detailed description' and the 'claims'.

DETAILED DESCRIPTION

Figure 1:
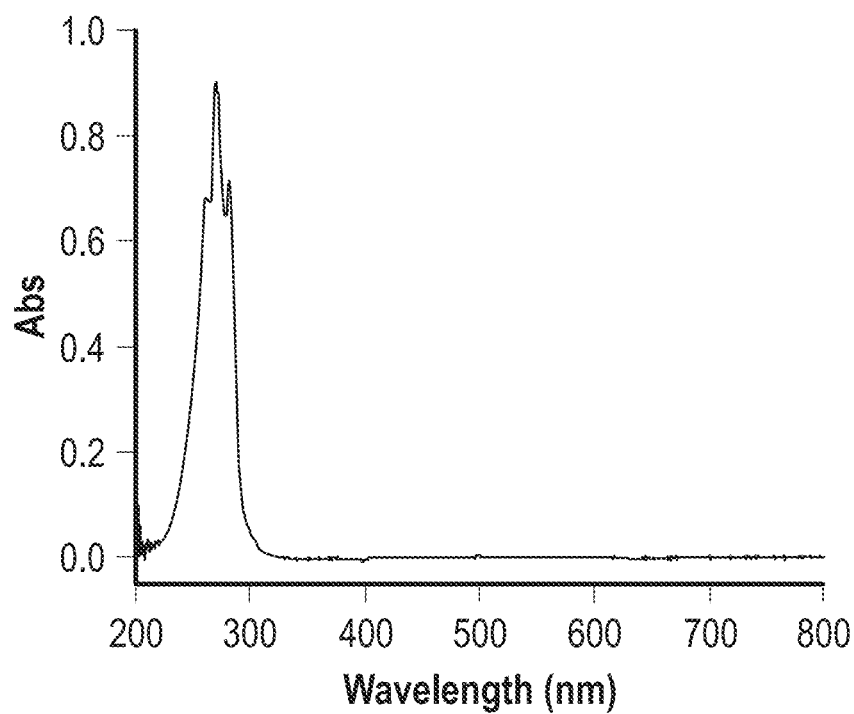
FIG. 1: Depicts the UV absorption spectra of AgNPs complex with ESA.

Geographical Origin:
Tung tree (*Aleurites fordii, Vernicia fordii* (family: Euphorbiaceae)) is a species of *Vernicia* is a native woody oil plant in subtropical areas of China. It belongs to the spurge family also found in Burma, northern Vietnam. Tung tree was introduced to the United States in 1904 and grown mainly in the Southern regions of the United States. It is a small to medium-sized deciduous tree growing to 20 m tall, with a spreading crown. The bark is smooth and thin. The leaves are alternate, simple, 4.5-25 cm long and 3.5-22 cm broad, heart-shaped or with three shallow, maple-like lobes, green above and below, red conspicuous glands at the base of the leaf, and with a 5.5-26 cm long petiole. The flowers are 2.5-3.5 cm diameter, with five pale pink to purple petals with streaks of darker red or purple in the throat. The fruit is a hard, woody pear-shaped berry 4-6 cm long and 3-5 cm diameter, containing four or five large, oily seeds; it is green initially, becoming dull brown when ripe in autumn.

Tea tree: *Melaleuca alternifolia*, commonly known as tea tree is a species of tree or tall shrub in the myrtle family, Myrtaceae. Endemic to Australia, it occurs in southeast Queensland and the north coast and adjacent ranges of New South Wales where it grows along streams and on swampy flats, and is often the dominant species where it occurs. It is a small tree to about 7 m (20 ft) with a bushy crown and whitish, papery bark. The leaves are arranged alternately, sometimes scattered or whorled. The leaves are smooth, soft, linear in shape, 10-35 mm (0.4-1 in) long and 1 mm (0.04 in) wide. The Flowers occur in white or cream-colored masses of spikes 3-5 cm (1-2 in). The small woody, cup-shaped fruit, 2-3 mm (0.08-0.1 in) in diameter are scattered along the branches.

*Aloe vera* (*Aloe barbadensis*): It is a succulent plant species of the genus *Aloe*. An evergreen perennial, it originates from the Arabian Peninsula, but grows wild in tropical, semi-tropical, and arid climates around the world. It is cultivated for agricultural and medicinal uses. *Aloe vera* is a stem less or very short-stemmed plant growing to 60-100 cm (24-39 in) tall, spreading by offsets. The leaves are thick and fleshy, green to grey-green, with some varieties showing white flecks on their upper and lower stem surfaces. The margin of the leaf is serrated and has small white teeth. The flowers are produced in summer on a spike up to 90 cm (35 in) tall, each flower being pendulous, with a yellow tubular corolla 2-3 cm (0.8-1.2 in) long.

Soybean: The soybean or soya bean (*Glycine max*) of the family Fabaceae is a species of legume native to East Asia, widely grown for its edible bean, which has numerous uses. The fully mature soybean plants are generally between 51-127 cm (20-50 inch) in height and have rooting depths between 76-152 cm (30-60 inch). Soybeans form inconspicuous, self-fertile flowers which are borne in the axil of the leaf and are white, pink or purple. The fruit is a hairy pod that grows in clusters of three to five, each pod is 3-8 cm (1.2-3.1 inch) long and usually contains two to four (rarely more) seeds 5-11 mm in diameter.

Mustard seeds: Mustard seeds are the small round seeds of various mustard plants. The seeds are usually about 1 to 2 millimetres in diameter and may be colored from yellowish white to black. They are an important spice in many regional foods and may come from one of three different plants: black mustard (*Brassica nigra*), brown Indian mustard (*B. juncea*), or white/yellow mustard (*B. hirta/Sinapis alba*). The mustard plant is a plant species in the genera *Brassica* and *Sinapis* in the family Brassicaceae. Mild white mustard (*Sinapis alba*) grows wild in North Africa, the Middle East, and Mediterranean Europe, and has spread farther by long cultivation; oriental mustard (*Brassica juncea*), originally from the foothills of the Himalaya, is grown commercially in India, Canada, the United Kingdom, Denmark, and the US; black mustard (*Brassica nigra*) is grown in Argentina, Chile, the US and some European countries.

Sunflower seeds: The sunflower seed is the fruit of the sunflower (*Helianthus annuus*). *Helianthus annuus*, the common sunflower, is a large annual forb of the genus *Helianthus* grown as a crop for its edible oil and edible fruits. The plant was first domesticated in the Americas. The plant has an erect rough-hairy stem, reaching typical heights of 3 metres. The leaves are broad, coarsely toothed, rough and mostly alternate. The "flower" of the sunflower which is actually a "flower head" or pseudanthium consists of numerous small individual five-petal flowers. The outer flowers, which resemble petals, are called ray flowers. Each "petal" consists of a ligule composed of fused petals of an asymmetrical ray flower. They are sexually sterile and may be yellow, red, orange, or other colors. The flowers in the center of the head are called disk flowers. These mature into fruit (sunflower "seeds"). The disk flowers are arranged spirally. Generally, each floret is oriented toward the next by approximately the golden angle, 137.5°, producing a pattern of interconnecting spirals, where the number of left spirals and the number of right spirals are successive.

Source:

The Tung seed oil, commonly known as China wood oil is purchased from Arista, USA.

The tea tree oil is procured from Rmayra Naturals Impex, Delhi.

Lauryl polyglucoside (Elotant Milcoside 200) is procured from LG Care, South Korea.

The *Aloe vera* extract is procured from Tri-K industries, USA.

The soya bean hydrolysate is procured from Tri-K industries, USA.

Glycerin derived from vegetable oil is procured from Virgoz oils and Fats PTE LTD., Singapore.

The 'instant and persistent' compositions described in the present invention comprise silver nanoparticles made from 'green' synthesis, carbohydrate based, biodegradable gelling agent, ethyl alcohol, fatty acids derived from Tung seed oil, water and optionally, skin benefit agents that are derived from renewable sources.

In an embodiment, the present invention discloses safe and environment benign sanitizing hydro-alcoholic gel composition for topical application with instant and persistent antimicrobial activity comprising of,
  a) 60-70% by weight of ethyl alcohol;
  b) 5 to 100 ppm by weight of silver nanoparticles;
  c) 0.2 to 5% by weight of fatty acids derived from Tung seed oil;
  d) 0.2 to 2% by weight of carbohydrate based gelling agents;
  e) optionally, 1 to 5% skin benefiting agents; and
  f) demineralized water to make up 100% w/w.

In an embodiment, the hydro-alcoholic gel composition of the present invention comprises minimum 99% of 'natural origin' content as per the definition of ISO 16128-2.

In yet another embodiment, the hydro-alcoholic gel composition of the present invention provides long lasting or persistent anti-microbial cover that would last for at least four hours or more and thereby the 'sanitized' state of hands is maintained for prolong period.

Silver Nanoparticles (AgNPs) and its Application as Antimicrobial

Silver nanoparticles (AgNPs) are well established for their antimicrobial properties. The antimicrobial property has been exploited in the fields of personal hygiene, hospital acquired infections (nosocomial infections), biomedical devices, textiles, food packaging, animal husbandry and purification of air and water (filters) (Delekar et al.; *Materials Science and Engineering C* 97, 954-965 (2019)). Nose masks with silver nanoparticles are being used by people during current COVID-19 pandemic (example, reusable mask embedded with silver nanoparticles by Boomer Naturals).

Silver is far less toxic to the environment and other living creatures compared to other antimicrobials that are typically chlorinated organic molecules for examples, p-chlorometaxylene (PCMX), Triclosan, Triclocarban (TTC) and chloromethylisothiazolinone (CMIT). In addition to being environmentally benign, AgNPs are stable, cost effective and they work equally well after being immobilized on textile fabric, ceramic or plastic.

Use of silver for treating burn wounds and for avoiding sepsis is the most remarkable application. Silver is also combined with drugs (for ex. silver-sulphadiazine, silver-tetracycline) that are used in healing of ulcerous wounds and burn wounds. Several wound dressing products containing silver nanoparticles are available in the market. One such example of commercial wound dressing is 'Acticoat'. Other examples of dressings and gels for treating wounds are Silva Kollagen gel, Aquacel Ag Advantage, UrgoTul Ag, Polymem Silver Finger Toe dressing and Opticell Ag+. Silver based dressings are known for sustained release of drug, rapid killing of broad spectrum of bacteria with a particular effectiveness against some of the antibiotic resistant bacteria as in Methicillin resistant *S. aureus*, and Vancomycin resistant *Enterococcus*.

Paknikar et al. reported a hydrogel using silver nanoparticles (AgNPs) for topical applications including wound treatment (*Molecular Pharmaceutics, Vol.* 6, NO. 5, 1388-1401, 2009). This polyacrylate gel with AgNPs also showed anti-inflammatory effect. Paknikar et al. demonstrated that the gel formulation with AgNPs at low concentration is not only an effective antimicrobial but a safer alternative to conventional topical antimicrobial agents particularly for treating burn wounds. This product is marked by Khandelwal Labs, Mumbai, as 'Silveron-Gel'.

Australian patent (AU322839 (2012)) teaches use of silver particles in compositions for treating skin infections wherein the particle has metallic silver as the interior and metal oxide as the exterior. Such particles are used with other silver compounds like silver-berberine and silver-tetracycline. These compositions are used for treating all types of skin infections.

EP3177142 (2018) teaches how to overcome the problem of agglomeration of colloidal silver nanoparticles by immobilizing them on porous inorganic substrates like zinc oxide, calcium carbonate or magnesium hydroxide. This immobilization silver particle also addresses aesthetic disadvantage due to the color of nanoparticles Immobilized nanoparticles are said to exhibit antimicrobial efficacy comparable to colloidal AgNPs and are suitable for personal care products.

Another recent application (US20180133124 A1) by Bio-Gate discloses body care product compositions containing porous silver particles. These porous particles are made from alloys of silver-zinc or silver-zinc-copper wherein silver is the major element. The particle size is said to be between 1 to 100 microns to avoid any possible cytotoxicity issue that might arise from nano-sized silver. These porous micro particles are reported to release the 'just adequate' amount of silver needed for antimicrobial action, thus avoiding the higher concentrations that can result in undue cytotoxicity.

Yet another application of immobilized AgNPs taught by DE 60022344(2006) is in tooth brushes and baby pacifiers.

As mentioned in the background section, the antimicrobial properties of AgNPs are now extended to hydro-alcoholic gel formulations for sanitization of hands. Nano Japan has a product in Japan and Singapore with polyethylene polymer and AgNPs in hydro-alcoholic gel system. This composition uses polyethylene (thin plastic like) film for persistent effect. However, the use of plastic like film of polyethylene is big concern for the biodegradability and equally concerning is the non-renewable origin of the polymer.

The present invention discloses the use of biodegradable vegetable carbohydrate type of gelling agents along with fatty acids derived from Tung seed oil (*Aleurites fordii*, oil from seeds) and silver nanoparticles, produced by 'Green' synthesis accomplished by vegetable derived surfactant.

Green Synthesis of Silver Nanoparticles (AgNPs)

Silver nanoparticles are synthesized by 'Green' process recently reported by Koshti et al. (IN 316500 (2019)). It is a very efficient method for producing silver nanoparticles using a bio-based 'Green' surfactant, alkyl polyglucoside (APG) of formula I, manufactured from dextrose and fatty alcohol which in turn is derived from vegetable oils.

Formula I

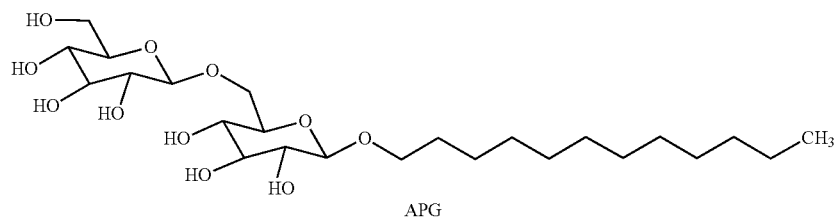

APG

These non-ionic 'Green' bio-based surfactants act as reducing agents as well as stabilizing/capping agents for the newly synthesized AgNPs. APG, a bio-based surfactant from renewable vegetable source is a commercially viable methodology to produce AgNPs since this 'green' synthesis obviates concerns regarding disposal of the biomass that is associated with process involving microbes.

In present invention, AgNPs are synthesized from commercially available APG as per the process of IN316500 and this stock solution in water (2000 ppm) (Example 1) is used for creating the topical hydro-alcoholic gel formulations of Table 5.

If necessary, the stock solution may further be diluted with water to create solution with concentration of 100 ppm of AgNPs.

The SPR (Surface Plasmon Resonance) of the colloidal AgNPs (2000 ppm) is around 413 nm, the average particle size as measured by HR-TEM analysis and Dynamic Light Scattering (DLS) is 15 nm and 55 nm respectively and zeta potential is found to be −24 mV (Example 1). DLS analysis measures the particle size with the hydrodynamic radius and it is always higher than the TEM analysis that measures the metal particles not having the hydrosphere around it. TEM analysis shows the nanoparticles are spherical. (TEM and DLS details are given in the experimental section). Zeta potential of −24 mV shows the stability of the colloid.

Carbohydrates Based Biodegradable Gelling Agents:

Most of the sanitizing alcohol based hydro-alcoholic gels are made from acrylate type of polymers, commonly known as 'carbomers'. These gelling agents are cross-linked sodium salts of synthetic poly acrylic acids or copolymers of acrylic acid salts and alkyl acrylates. The cross-linked acrylate polymers enjoy the unique status in lower alcohol (ethanol or isopropanol) based hand sanitizers. However, from the point of view of sustainability and eco-safety, it is important that one should do away with the synthetic polymers like carbomers (carbopols) that are not easily biodegradable and whose manufacturing involves hazardous and flammable solvents.

In view of these limitations of carbomer, the gelling agents that are used for the compositions of the present invention are based on renewable and biodegradable carbohydrates. Carbohydrates derived from vegetables can be used with little or no modification. Examples of such carbohydrate based gelling agents that are commercially available are cellulose derivatives like methyl cellulose (Benecel EM from Ashland) carboxymethyl cellulose, hydroxylpropyl methyl cellulose (Methocel E4M Dow, Methocel 40-0202, Dow), hydroxyl propyl cellulose (Klucel G, Ashland), hydroxyethyl cellulose (Natrosol 250 HHX/HHR/HBR, Ashland), sodium alginate, hyaluronic acid sodium salt, xanthan gum and carrageenan. All these carbohydrate based gelling agents yield transparent or translucent gels in water. The incorporation level of these carbohydrate based gelling agents varies depending upon the molecular weight and the targeted viscosity for the hydrogels. It also depends on the ratio of alcohol to water in the final hydrogel formulation. The challenge of getting reasonable viscosity in compositions containing higher percentage of alcohol (60 to 75) is addressed by increasing the incorporation level of carbohydrate gelling agent.

In an embodiment, the carbohydrate gelling agents for making hydro-alcoholic gel composition of the present invention varies from 0.2% to 2% (Table 5). The acid form of carbohydrate gelling agents can be used after the neutralization with inorganic base like sodium/potassium hydroxide (for example, hyaluronic acid or alginic acid).

In another embodiment, the process for making the hydro-alcoholic gel comprises soaking the suitable vegetable carbohydrate based gelling agent/thickener such as hydroxyl ethyl cellulose, hydroxyl propyl cellulose or hyaluronic acid or its salt in water for several hours. To this 'soaked' gelling agent, ethyl alcohol is added under stirring at room temperature. The pH of the whole mix is adjusted to 6.5 to 7.5 using either sodium hydroxide or citric acid. The other ingredients of the present composition such as AgNPs solution, skin benefiting agent of natural origin, fatty acids of Tung seed oil are added in any sequence. Viscosities of hydro-alcoholic gels depend on the amount of gelling agent, amount and ratio of water to alcohol and the type of gelling agent and its average molecular weight. The viscosity of the final gel formulation may vary from 200 cps to 2000 cps.

Skin Benefiting Agent:

Natural or nature-derived skin benefit agents of hydro-alcoholic gel formulations are selected from the group of emollients, moisturizers, natural antimicrobials and amino acids of NMF (Natural Moisturizing Factor) of stratum corneum, oligo-peptides or small peptides or amino acids derived from vegetable protein. Examples of such commercially available protein derivatives from vegetables are soya seeds, sunflower seeds, wheat, rice, quinoa, barley, peas, and baobab etc. Simple glycols or diols or triols derived from vegetable renewable source may be used as skin benefit agent in the present composition. For example, 1,3-propane diol derived from carbohydrate or glycerin from vegetable oils such as soyabean oil, mustard seed oil, sunflower seed oil can be the moisturizers of gel compositions of present invention. Any skin benefiting agent that is derived from renewable source may be added. A variety of essential oils (peppermint, thyme, lemon grass, citronella, rosewood, rosemary, lavender, cinnamon oil, cider wood, sandal wood oil etc.) may be used as skin benefiting agents in the present composition. Skin beneficial oils include Tea tree oil (*Melaleuca alternifolia*), citrus medica peel oil, herbal extracts including Neem leaf extract (Azadirachta indica), *Aloe vera* (*Aloe barbandensis*), coriandar, nutgrass, Vetiver grass, and grapefruit seed extract. A variety of esters of glycerin with fatty acids derived from vegetable oils may be included in the formulations of the present invention, for example, cocomono glycerides or caprylic capric triglyceride. Any emollient like polyethylene glycol-7 glyceryl cocoate (PEG-7 glyceryl cocoate) can be part of the hydro-alcoholic gel formulations provided ethylene oxide is sourced from vegetable carbohydrates and not from petrochemical route. Any skin benefit agent (for moisturizing, for antimicrobial derma purification like capryloyl glycine and undecylenoyl glycine, for anti-inflammatory, for soothing, and for nutrition etc.) derived from renewable sources and which is soluble in hydro-alcoholic mixture may be used in the compositions of present invention. Table 5 shows examples with soya protein hydrolyzate, glycerin, Tea tree oil and *Aloe vera* (leaf juice) as skin benefit agents.

Evaporation of ethyl alcohol takes away the moisture of stratum corneum and hence any moisturizing agent and an emollient of natural origin is useful to counter the drying effect of ethyl alcohol.

Application of the topical hydro-alcoholic gels of the present invention described in Table 5 comprising the aforesaid skin benefiting agents prevents the excessive dryness resulting from frequent application of hydro-alcoholic sanitizer of the art.

Fatty Acids of Tung Seed Oil:

Fatty acids used in the compositions of the present invention are derived from Tung seed oil. Tung seed oil is obtained by the seeds of the nuts of Tung tree (*Aleurites fordii, Vernicia fordii* (family: Euphorbiaceae)). It is commercially available and is commonly known as China wood oil. The oil forms a hydrophobic film on the surface. This behavior is known as drying property and Tung seed oil exhibits this film forming (drying) property when exposed to air due to the reaction of its fatty alkyl chain component with the atmospheric oxygen forming ether linkages between the doubly bonded carbons of alkyl chains of triglycerides. This intra-molecular (linking of alkyl chains of same triglyceride molecule) or inter-molecular ether linkage is akin to the cross linking of macromolecules in polymer chemistry, ultimately yielding a polymeric film. The typical fatty acids of triglycerides of Tung seed oil comprise of majorly α-Eleostearic acid (CAS 506-23-0), Linoleic acid (CAS 60-33-3), Palmitic acid (CAS57-10-3) and Oleic acid (CAS 112-80-1). The composition typically has α-Eleostearic acid in upwards of 80% and other unsaturated fatty acids. The total unsaturated fatty acids are around 95%.

Major component of fatty acids of Tung seed oil is α-Eleostearic acid (ESA), a poly-unsaturated fatty acid (PUFA). ESA has three double bonds (9 Z, 11E, 13 E) and has a pair of conjugated double bonds that makes it highly reactive. It is important to note that conjugated long chain fatty acids are reported to have anticancer properties for cancers of mammary glands, colon and skin (Belury M. A.; Inhibition of carcinogenesis by conjugated linoleic acid: potential mechanisms of action. *J. Nutr.;* 132: 2995-8; 2002). ESA also occurs in seeds of Bitter Gourd which is consumed by human race since time immemorial. ESA is reported to possess anti-inflammatory properties (Pubali Dhar et al.; *Nanomedicine*, Vol. 14, No. 5, 2019). ESA has been shown to ameliorate (https://doi.org/10.1371/journal.pone.0024031, Bevan et al. August 2011) inflammatory bowel disease in animals via dietary route. Korean scientists recently reported ESA in cure of breast cancer. They established the mechanism of suppression of cancer cell by ESA (*Cancer Science*, 2010; 101: 396-402).

In addition to ESA, the minor components of Tung seed fatty acids are palmitic acid, oleic acid, and linoleic acid. These fatty acids occur in many other edible oils that are consumed by human race.

Figure 8:
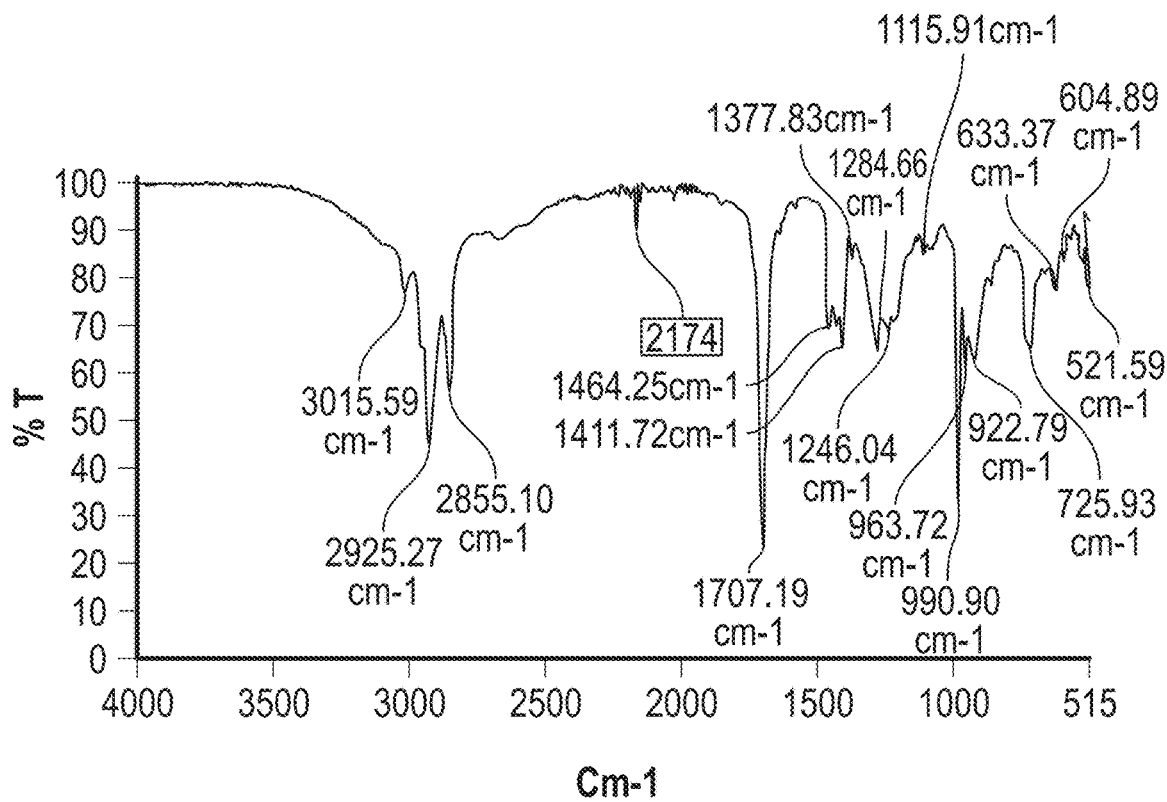
FIG. 8: Depicts IR spectrum of fatty acids of Tung seed oil.

The 'whole' (unfractionated) of fatty acids of Tung seed oil that are used in the present invention are obtained by saponification of Tung seed oil (alkaline hydrolysis) and isolation of fatty acids after acidifying the alkaline hydrolysate. The 'whole' fatty acids are washed with water to free it from any acidity of mineral acids that are used for the acidification (The saponification process and isolation of 'whole' of fatty acids is described in detail in Example 2). The whole of Tung seed oil fatty acid, a mixture of fatty acids (chromatography results for alkyl chain distribution are given in Example 2), is a low-melting pale yellow colored solid with a very good UV absorbing properties arising out of conjugation of ESA (E1% 1 cm is around 1600 at 270 nm (Example 2). The unfractionated fatty acids of Tung seed oil show the characteristic IR frequency of 1707 $cm^{-1}$, 995 $cm^{-1}$ (FIG. 8). The reason for unfractionated fatty acids being a low melting solid instead of a liquid is the presence of two double bonds ESA (major component of whole mix) with 'trans' geometry. Proton magnetic resonance spectrum (400 MHz, $CDCl_3$) details are given in Example 2 wherein the coupling constants (J) and the splitting pattern for protons of trans geometry can be distinguished from the coupling constant for cis geometry of double bonds.

Figure 10:
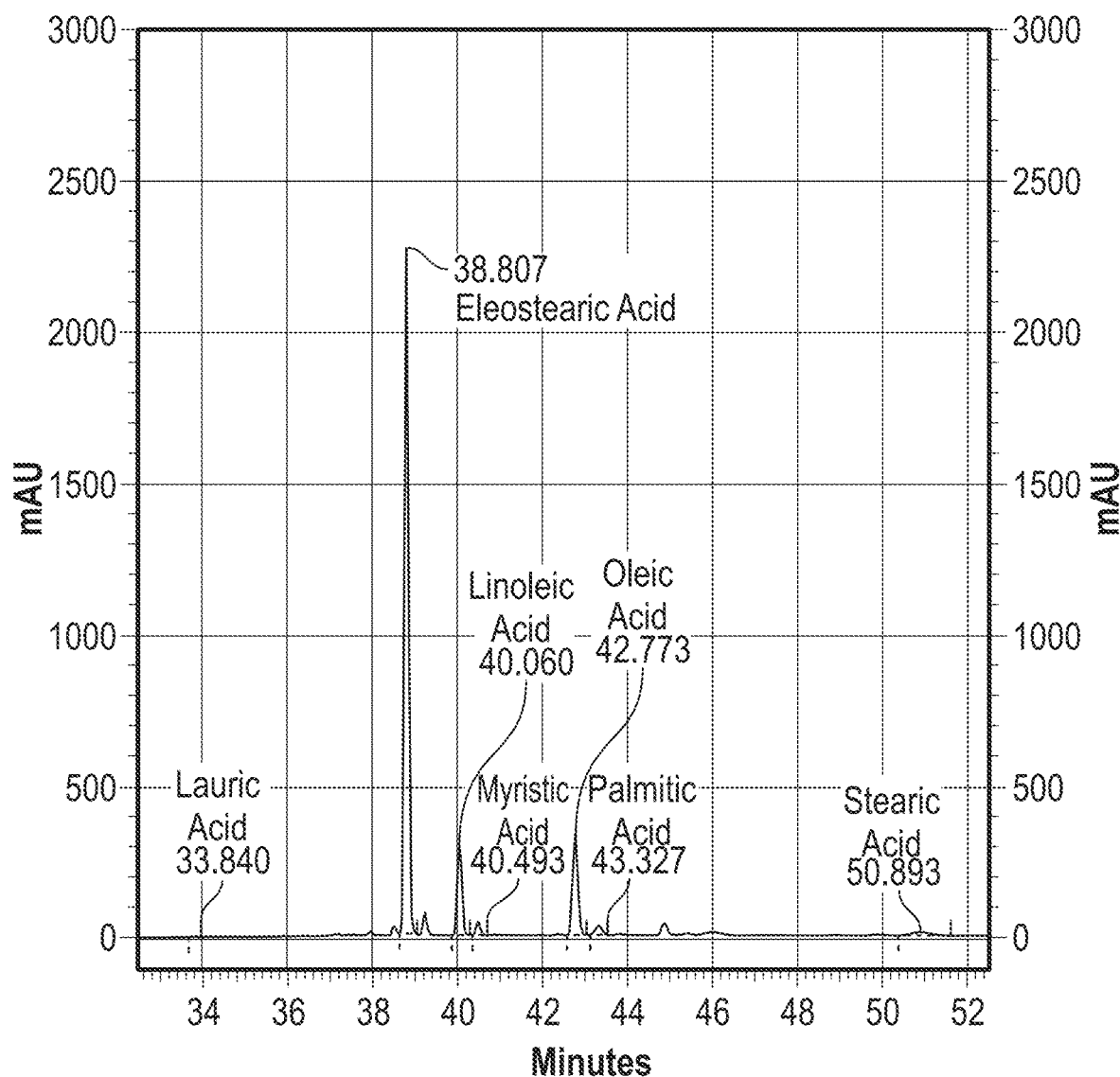
FIG. 10: Depicts the chromatogram of fatty acids distribution of Tung seed oil.

The fatty acid distribution is determined by chromatography (FIG. 10). It can be done by converting fatty acids into a volatile derivative like methyl ester or silyl ester. Another convenient way of doing chromatography is HPLC, particularly for thermo-sensitive molecules like ESA. The fatty acids of Tung seed oil are resolved by 'reversed phase' chromatography using water-acetonitrile gradient system. Chromatogram and the chromatographic conditions are given in Experimental section (Example 2). The analysis of hydrolyzed commercial Tung seed oil does show ESA to be around 82%. The C18 acids have been oleic and linoleic, around 6% each. The saturated fatty acids are found to be around 4%.

Fatty Acids of Tung Seed Oil for Re-Fatting and Moisturizing Benefit:

Fatty acids and oils containing saturated or unsaturated alkyl chains are almost integral part of personal care products. The various types of lipids are part of the skin, particularly the upper layer of skin, the stratum corneum. In a cleansing process many times excessive removal of constituent lipids results into drying of skin. This drying of skin has serious consequences. The loss of lipids from stratum corneum leads to increased rate of loss of moisture. This ultimately results into itchiness of skin to chapping/cracking of skin. To overall moisturize and retain the moisture balance of skin by replacing lost lipids, oftentimes oils and fatty acids are included in all skin and hair care products. Fatty acids and oils of coconut, soy seed, sunflower seed, safflower seed are some of the most commonly used as moisturizers. The fatty acids of Tung seed oil like any other fatty acids can be used to restore the lost lipids (during the cleansing process by surfactants) of stratum corneum in the compositions of the present invention.

Fatty Acids of Tung Seed Oil as UV-Protector for the Formulation Ingredients as Well as UV Protector for Hair and Skin.

Fatty acids of Tung seed oil have good UV absorbing power as is evident from its conjugated system and from its E1% 1 cm of 1600 at 270 nm and 360 at 290 nm. These UV absorbing fatty acids can not only protect the ingredients of the formulations but also the skin and hair from the ravages of solar radiation when the formulations are applied. The fatty acids of Tung seed oil absorb in the UV B region significantly as evident from its E1% 1 cm value of 360 at 290 nm (FIG. 1). UV B radiation of solar spectrum is the most damaging since it causes skin cancer.

The UV absorption power of fatty acids of Tung seed oil is more than double of popular UV absorbers like Homosalate and Octyl salicylate as can be seen from the molar extinction coefficients (t) and E1% 1 cm. Both homosalate and Octyl salicylates are popular sunscreen molecules all over the world.

TABLE 1

| UV absorbing compounds | $\lambda_{max}$ | E1 % |
| --- | --- | --- |
| Fatty acids of Tung seed oil | 290 nm | 360 |
| Homosalate (118-56-9) | 305 nm | 180 |
| Octyl salicylate (118-60-5) | 305 nm | 165 |

Antimicrobial Efficacy of the 'Whole' Fatty Acids of Tung Seed Oil

The 'whole' of fatty acids of Tung seed oil exhibits a broad spectrum of antimicrobial activity. It shows decent activity against representative Gram negative bacteria (*Escherichia coli, Pseudomonas aeruginosa, Burkholderia cepacia*), Gram positive bacteria (*Staphylococcus aureus, Propiniobacterium acnes*) yeast (*Candida albicans, Malassezia furfur*) and mold (*Aspergillus niger*) as is evident form the minimum inhibitory concentrations given in Table 2 below.

Minimum Inhibitory Concentration of Tung Seed Fatty Acids

TABLE 2

| Microorganism | MIC of Example 2 (%) |
| --- | --- |
| *Staphylococcus aureus* ATCC 6538 | 0.6 |
| *Pseudomonas aeruginosa* ATCC 15442 | 0.8 |
| *Burkholderia cepacia* ATCC 25416 | 0.8 |
| *Escherichia coli* ATCC 8739 | 0.5 |
| *Candida albicans* ATCC 10231 | 0.5 |
| *Aspergillus niger* ATCC 16404 | 0.8 |
| *Propiniobacterium acnes* MTCC 1951 | 0.5 |
| *Malassezia furfur* MTCC 1374 | 0.8 |

Fatty acids of Tung seed oil and silver nanoparticles Fatty acids of Tung seed oil are surprisingly found to complex with AgNPs when both are mixed in hydro-alcoholic medium. This is due to the presence of olefinic bonds and suitable geometry in polyunsaturated fatty acids. As mentioned above, the fatty acids of Tung seed oil contain over 80% α-Eleostearic acid (ESA) which has three double bonds at 9Z, 11E and 13E positions and it acts as a ligand for silver metal via carboxylic acid group and via olefinic double bonds whenever stereochemistry permits (Formula II).

Formula II

Ag-ESA complex

Figure 2:
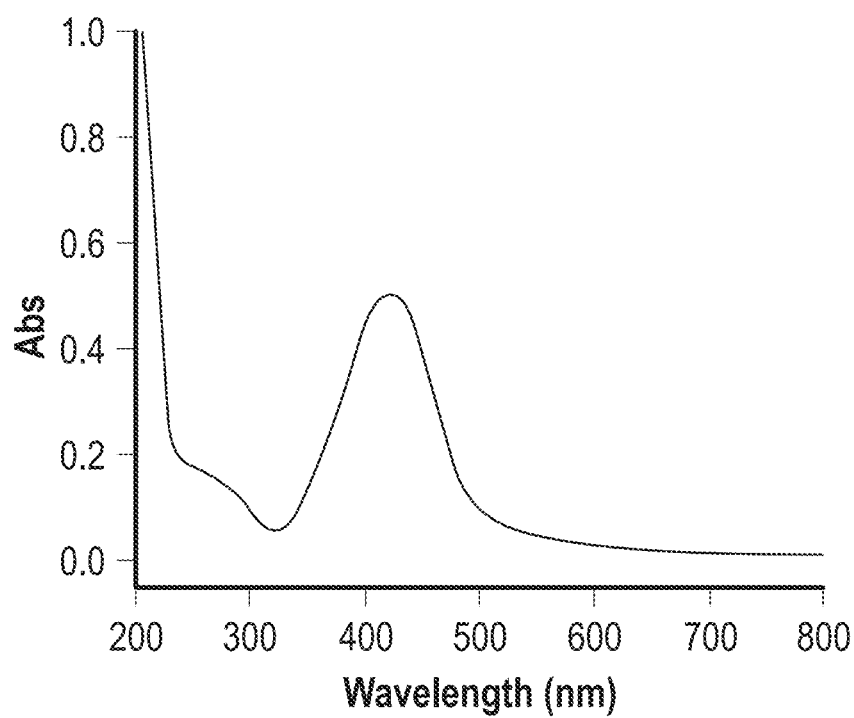
FIG. 2: Depicts the surface plasmon resonance (SPR) for AgNPs in hydro-alcoholic solution.
Figure 3:
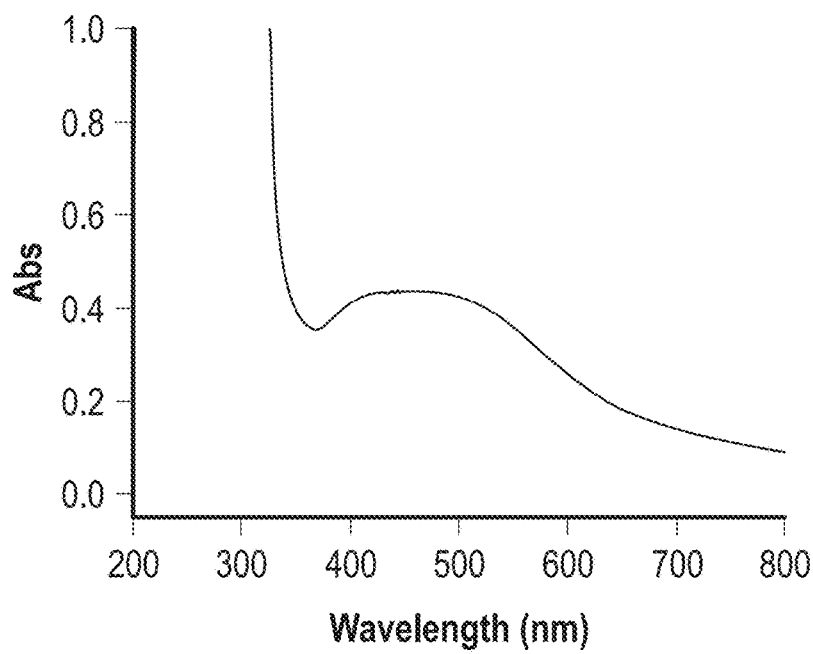
FIG. 3: Depicts the changes in SPR pattern for AgNPs upon complexation.

ESA absorbs strongly around 270 nm and does not absorb beyond 300 nm (FIG. 1). Surface plasmon resonance (SPR) for AgNPs made as per the procedure of Example 1, is at 413 nm (FIG. 2) measured in hydro-alcoholic solution. On addition of ESA to this hydro-alcoholic solution of AgNPs, the UV absorbance pattern completely changes and this can be attributed to π complexation between olefinic double bonds and silver metal and the shift towards red (FIG. 3). Thus, the π complexation is clearly seen by shifting SPR of AgNPs from 413 to 460 nm. This color change due to complex formation is seen visibly as well.

The hydro-alcoholic gel formulations of present invention deploy fatty acids of Tung seed oil in the range of 0.2 to 5% of the total gel formulation which is in far excess of concentration of silver nanoparticles. AgNPs are deployed at concentration below 100 ppm (typically 5 to 25 ppm) whereas fatty acids of Tung seed oil are present at concentration of 2000 ppm to 50,000 ppm. Thus, part of the unsaturated fatty acids forms π complexes with metallic silver as depicted in FIG. 3.

Figure 5:
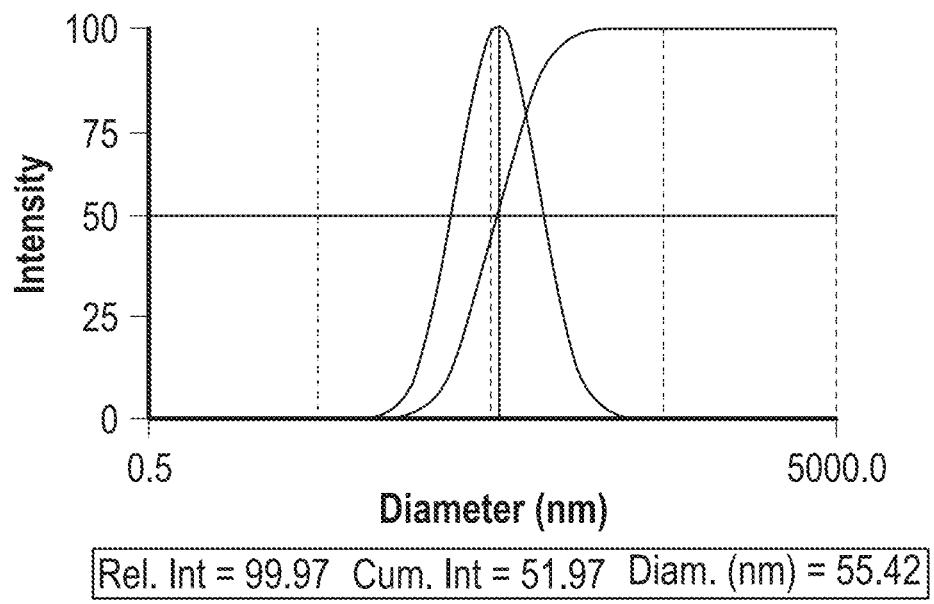
FIG. 5: Depicts the Particle size analysis of Silver nanoparticles using Brookhaven Instruments of example 1.
Figure 6:
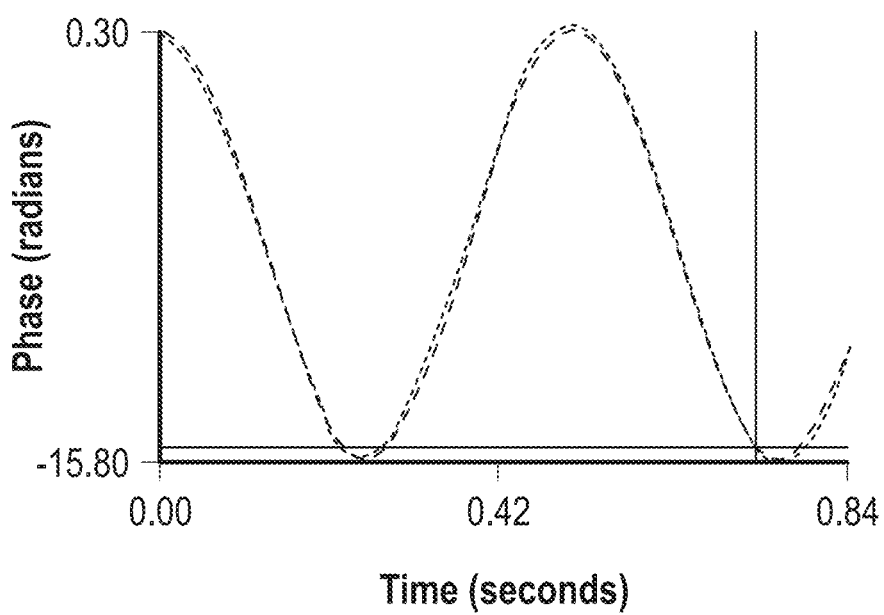
FIG. 6: Depicts zeta potential of Silver nanoparticles of example 1.
Figure 7A:
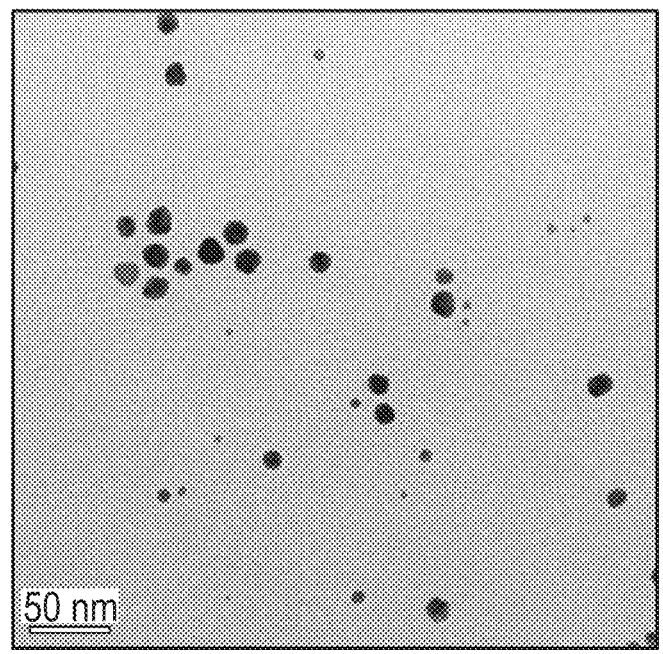
FIGS. 7A and 7B: Depicts the Transmission Electron Microscopy of Silver nanoparticles (TEM) performed on HR-TEM 200 Kv.
Figure 7B:
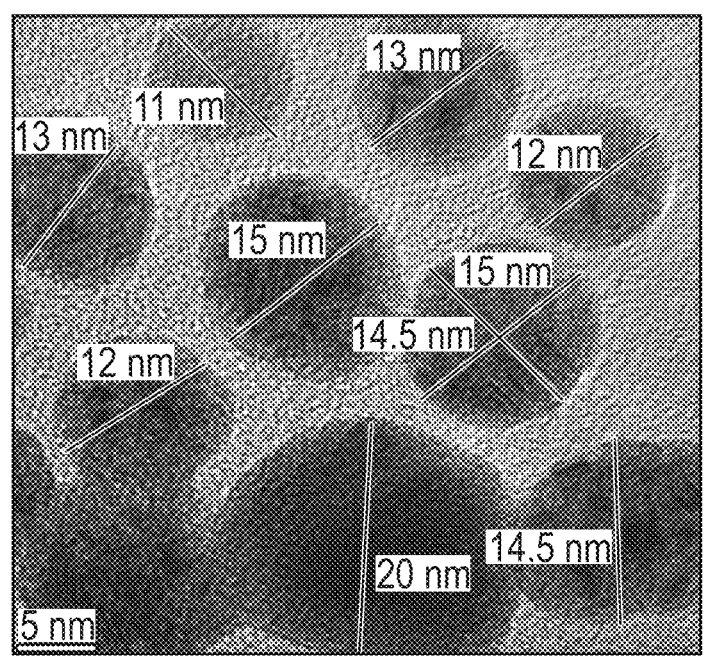

Also, shift in the SPR towards red is also an indication that particle size is getting bigger. AgNPs of Example 1 have hydrodynamic size of 55 nm according to, Dynamic Light Scattering Analysis (FIG. 5) and actual size of nanoparticles is 15 nm as per Transmission Electron Microscopy (FIG. 7, Example 1).

When silver nanoparticles are mixed with fatty acids of Tung seed oil in hydro-alcoholic solution, it is observed that the UV absorbance pattern completely changes. In addition, the hydrodynamic size of the silver particles is increased from 55 nm (Example 1) to 158 nm (Example 4). This can be attributed to the complexing of ESA to silver particles where the fatty acids of Tung seed oil are acting like ligands (Example 4, hydro-alcoholic solution of 5 ppm of AgNPs with 3% of Fatty acids of Tung seed oil).

In the ESA-Ag π complex, ESA acts as ligands and stabilizes the silver nanoparticles by preventing the aggregation of particles. This ligation where olefinic bonds donate π electrons thereby keeps metallic silver in its zero oxidation state. Oxidized form of silver ion ($Ag^+$) is very reactive and reacts with the traces of chloride ions in water of the formulation and precipitates out as black particulate (AgCl) matter. Thus, ESA stabilizes silver nanoparticles by ligation, thereby preventing aggregation and oxidation of metallic silver. The excess of ESA serves as antimicrobial hydrophobic protectant on the skin of hands when applied through the present hydrogel formulation. On exposure to air, the dieneic double bonds react with atmospheric oxygen to form hydroperoxide which then reacts with unsaturation of another alkyl chain to create crosslinking between two alkyl chains via an ether linkage. This is the well-established mechanism of drying phenomenon of drying oils (Ned A. Porter, Sarah E. Caldwell, Karen A. Mills "*Mechanisms of free radical oxidation of unsaturated lipids*" Lipids 1995, volume 30, Pages 277-290). Just like drying oils, the free fatty acids derived from these drying oils show similar behavior of drying ('film formation') upon exposure to atmosphere. This is easily demonstrated by spraying hydro-alcoholic solution of fatty acids of Tung oil on a petri-dish and keeping it at 37° C. (human body temperature) and observing the film formation. The film is formed by cross linking of fatty alkyl chains (hydrocarbon chain of 18 carbons) and hence completely hydrophobic.

Thus, the fatty acids of Tung seed oil in the present 'no-rinse' hydro-alcoholic sanitizer composition provide antimicrobial protection, exhibits the property of re-fatting the lost lipids, forms a hydrophobic coat on the human hands and protects them from getting removed by friction or by water, forms the complex with AgNPs and immobilizes silver thereby preventing it from getting oxidized and also prevents nano-sized silver's penetration (percutaneous absorption) through the skin.

Preparation of Hydro-Alcoholic Gels with Vegetable Derived Gelling Agents.

The hydro-alcoholic gels of the present invention are prepared with gelling agents that are derived from vegetable origin, e.g. cellulose, hyaluronic acid or other carbohydrates. Accordingly, the process comprises soaking of vegetable derived carbohydrate in water for a few hours followed by adding all other ingredients (ethyl alcohol, skin benefit agents, fatty acids of Tung seed oil) and stirring it gently at room temperature. The concentration of gelling agents is adjusted to yield final viscosity in the range of 200 to 2000 cps.

The Present Compositions:

Composition II to Composition V contains both AgNPs and the fatty acids of Tung seed oil. Composition I have only AgNPs and Composition VI has only fatty acids of Tung seed oil whereas Composition VII is without both antimicrobials. Compositions I to VII are used to explain the microbiological outcome of the 'persistent' effect. Composition VIII and Composition IX depict complete formulations with other skin benefit agents.

The compositions of Table 5 containing both AgNPs and fatty acids of Tung seed oil are stable and no aggregation or oxidation of silver nanoparticles is observed as judged by UV absorbance after three months period at 25° C.

TABLE 5

| | Comp. I | Comp. II | Comp. III | Comp. IV | Comp. V | Comp. VI | Comp. VII | Comp. VIII | Comp. IX |
|---|---|---|---|---|---|---|---|---|---|
| Ethyl alcohol | 70 | 70 | 70 | 70 | 70 | 70 | 70 | 65 | 65 |
| Hydroxy propyl cellulose | 1.5 | 1.5 | 1.5 | | 1.5 | 1.0 | 1 | | 1 |
| Sodium hyaluronate | | | | | | | | | 1.0 |
| Hydroxy ethyl cellulose | | | | | | | | 2.0 | |
| AgNPs | 10 ppm | 10 ppm | 25 ppm | 10 ppm | 10 ppm | | | 25 ppm | 25 ppm |
| Fatty acids of Tung seed oil | | 1 | 1 | 2.0 | 3.0 | 3.0 | | 2.0 | 2.0 |
| Glycerin | | | | | | | | 3 | 3 |
| Tea tree oil | | | | | | | | 0.2 | 0.2 |
| Aloe Vera leaf extract | | | | | | | | 0.2 | 0.2 |
| Soya protein hydrolyzate | | | | | | | | 0.2 | 0.2 |
| Water | To make 100 | To make 100 | To make 100 | To make 100 | To make 100 | To make 100 | To make 100 | To make 100 | To make 100 |
| Viscosity | <1000 Cps | <1000 Cps | <1000 cps | <1000 Cps | <1000 cps | <1000 Cps | <1000 Cps | <1000 cps | <1000 Cps |
| Microbial growth (4 hours) Finger impression method | <20 CFU | <10 CFU | 2 CFU | 2 CFU | No colony | <20 CFU | TNTC | <10 CFU | <10 CFU |

Figure 4:
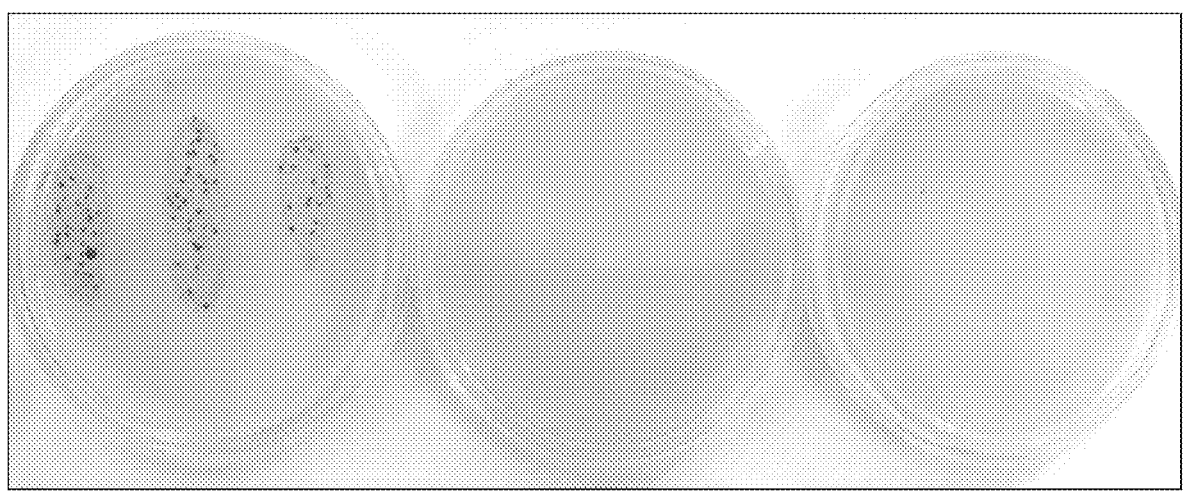
FIG. 4: Depicts the study of finger print impression before and after applying sanitizing gel (Composition V).

As can be seen from the Table 5, the hydro-alcoholic gel of composition I with AgNPs alone at 10 ppm level does show drop in colony count taken after 4 hours of fingerprinting (explained in details in subsequent embodiments) compared to composition VII which is the 'blank' formula without any antimicrobial for 'persistent' protection. Composition II has same concentration of AgNPs (10 ppm) with 1% of fatty acids of Tung seed oil. This combination has resulted in significant reduction in the count of microbial colonies as demonstrated by the finger printing impression done after 4 hours. Increasing the concentration of AgNPs more than double (25 ppm) seems to improve the performance after 4 hours as evaluated by fingerprinting for composition III. Similar performance is exhibited by composition IV with lower concentration AgNPs (10 ppm) and relatively higher concentration of fatty acids of Tung seed oil (2.0%). Composition V seems to give good protection after four hours of application, as observed by the absence of bacterial colonies in fingerprinting impression (FIG. 4). Higher amount of Tung fatty acids (3.0%) seems to exhibit synergy between both antimicrobials, namely, silver particles and the fatty acids of Tung seed oil. But more importantly, the film forming nature of Tung fatty acid seems to protect the immobilized silver particles and also seems to prevent wearing off the protective layer on the hands due to friction that is experienced in the normal activity during the period of four hours. The hydrophobic film formed on the hands prevents the nanoparticles getting dislodged by friction or by sweat.

In a separate comparative experiment fatty acids of Tung seed oil of composition V are replaced with 3% stearic acid and it results in terms of bacterial colony count being close to composition I. Thus, fatty acids of Tung seed oil show synergy with silver nanoparticles in a variety of ways, forming π complex and immobilizing the metal particles on the surface of hands, and preventing them from getting removed by normal wear and tear of human activity and contributing towards the overall antimicrobial shield by its modest anti-bacterial activity.

Evaluation of Anti-Microbial Efficacy (Persistent Effect) of Hand Sanitizer Formulation by Finger Impression Method Fixed quantity of hydro-alcoholic gel of (Table 5, Compositions I to VII) is applied to hands the way sanitizing gels are applied. The gel is spread uniformly by rubbing the palms of the hands against each other. After four hours the finger impressions are taken to check if the remnant content left on the hands after alcohol is evaporated protects the palm's surface from getting re-contaminated. This technique of visual observation of bacterial growth from handprints (handprint culture before application of alcohol based sanitizer and handprint culture after alcohol based sanitizer is applied) has been adopted from literature protocol that is predominantly used to improve hand hygiene of health workers. [a] WHO guidelines on hand hygiene in health care, 2009; b) Alebaly et al. (2018) Influence of Handprint Culture Training on Compliance of Healthcare Workers with Hand Hygiene, Hindawi Interdisciplinary Perspectives on Infectious Diseases, Volume, Article ID 3727521, (https://doi.org/10.1155/2018/3727521); c) Ewoud Reilman, Joke G. Hagting et al. (2015) Towards an antimicrobial 'microglove' Scientific Reports, 5:16679, DOI: 10.1038/srep16679 (https://www.nature.com/articles/srep16679); d) Y. Yamamoto et al. in 'Usefulness of training in hand hygiene using full hand touch method for hospital staff'; *Japanese Journal of Infection Prevention and control*, vol. 30, no 4, pp 281-287, 2015.

Finger impression before application of sanitizer gel: Finger impressions are taken on the pre-prepared Nutrient Agar medium plates containing 1% Tetrazolium chloride (2, 3, 5-triphenyl-2H-tetrazolium chloride). The plates are opened in aseptic conditions (laminar air flow unit) to prevent accidental contamination. Finger impressions are taken for about 10 seconds and plates are covered with the lids and incubated.

Finger impression immediately (Zero hour) after the application of sanitizer gel: Hand sanitizer gel (2.0 g, Compositions I to IX, Table 5) is then applied uniformly by hand rub method. Alcohol evaporates in a few seconds and immediately finger impression is taken as described above. On incubation for 72 hours aerobically at 35° C., bacterial colony count is found to be zero, occasionally, one. Instant sanitization of hands seems to be effective due to 65 to 70% alcohol content of the gel compositions.

Finger impression four hours after the application of sanitizer gel: Hand sanitizer gels (2.0 g, Compositions I to IX, Table 5) are then applied uniformly by hand rub method. Alcohol evaporates in a few seconds and normal activity is resumed. The finger impression is taken after performing the normal office work or lab work for four hours by following the same protocol of opening the agar nutrient plates in laminar flow unit. The covered plates are then incubated aerobically at 35° C. for 72 hours.

The FIG. 4 of the petri-plates illustrates the study of composition V. The first plate in FIG. 4 shows the impression of fingers before applying the sanitizing gel. Microbial colonies are too numerous to count (TNTC). Redox indicator Tetrazolium chloride dye (TTC) helps with the visual observation. The second petri-plate shows microbial colonies that represent the status of fingers immediately after the application of sanitizer gel of composition V and show no colonies after incubation. Third plate shows the bacterial colony count after four hours of application of the sanitizing gel. During this period of four hours normal activity with hands is performed. It can be seen that in the third petri-plate no bacterial colonies are observed.

Evaluation of 'Water Repellency' Property of Hydro-Alcoholic Gels

Hydro-alcoholic gel of composition V of Table 5 containing 1% hydroxyl propyl cellulose, 3% of fatty acid of Tung oil and 10 ppm of AgNPs is applied to the surface of glass petri-dish and allowed it to dry at physiological temperature of 37° C. for two hours to form a film on the glass surface. Similarly, hydro-alcoholic gel of composition I of Table 5 (without the fatty acid of Tung seed oil) is applied to another petri-plate and allowed to dry for 4 h at physiological temperature. The petri-plates are then filled with water (10 mL) and gently swirled. The water-washing in the petri-dish is collected carefully by pipetting out in a volumetric flask. It is analyzed for 'leached' AgNPs content in water by ICP-OES (Thermo Scientific). The analysis reveals that the composition V retains 90% of the Ag whereas plate coated with composition I retains less than 10% of Ag that is originally incorporated, the rest 90% got accounted in water washings. This shows that fatty acids of Tung seed oil immobilize AgNPs by virtue of forming the π complex and by forming a film of fatty acids. When the alcohol based hydrogels are applied on hands, the hydrophobic film of fatty acids of Tung seed oil does not get washed away or removed by water or sweat. Thus, this water-resistant (water-repellent) film is not only a long-lasting one but it immobilizes the AgNPs thereby providing the antimicrobial shield for a long time after the volatile alcohol is evaporated. The film forming property at physiological temperature also prevents interaction of AgNPs with the upper layer of skin, the stratum corneum. Hydro-alcoholic gel compositions of the present invention not only hold the AgNPs by coordination π complex but also by hydrophobic film formation as a result of aerial drying mechanism.

Alternately, Tung seed oil may be used directly in place of fatty acids derived from Tung seed oil in hydro-alcoholic gel composition of the present invention for the same purpose of film formation. However, the aesthetics of hydro-alcoholic gel formulations is compromised in terms of transparency due to limited solubility of triglyceride oils. More importantly, due to limited solubility of Tung seed oil in hydro-alcoholic gel medium, the coordination chemistry (it-complex formation) does not happen effectively. Hydro-alcoholic disposable sanitizing gels of the present invention are very convenient to use and very effective in sanitizing one's hands as it covers all the surface without causing any other safety concerns (flammability) that are associated with other format like sprays. Alternatively, thin spray like formulation of alcoholic or hydro-alcoholic solution without gelling agent can also be prepared with AgNPs and fatty acid of Tung seed oil.

In an embodiment, in the use of hydro-alcoholic gels of the present invention, ethyl alcohol sanitizes the surface of hand and evaporates quickly during application (spreading) due to rubbing action of palms leaving behind a thin film of silver nanoparticles and fatty acids of Tung seed oil. On exposure to air, the unsaturated fatty acids of Tung seed oil get converted into macro-molecules (cross linking) at physiological temperature of 37° C. eventually giving antimicrobial protective film that holds the silver nanoparticles by forming π complexes with the available unsaturation sites. Fatty acids of Tung seed oil are far more reactive in terms of the drying mechanism at physiological temperature of 37° C. compared to other drying oils like Linseed oil or Walnut oil.

Hand sanitizing compositions of the present invention are long lasting due to the persistent effect achieved by combination of AgNPs and fatty acids of Tung seed oil. The hydro-alcoholic gel compositions of the present invention contains 1 to 100 ppm of AgNPs and 0.2 to 4.0% w/w of fatty acids of Tung seed oil and minimum 60% of ethyl alcohol.

Advantages of the Present Invention

1) 'Instant' and 'persistent' sanitizing gel compositions with natural antimicrobials: The instant sanitization of hand's surface is assured by ethyl alcohol content of the composition and the 'sanitized' state of hands is maintained for substantial period by silver nanoparticles that are immobilized by a film formed by the fatty acids of Tung seed oil. Both silver nanoparticles (AgNPs) and fatty acids of Tung seed oil show broad spectrum antimicrobial activity. The film formed by the fatty acids of Tung seed oil is water-repellant and doesn't get worn off by water/sweat or by friction (rubbing of hand's surface against another surface), thus forming an 'invisible glove' on the hand.

2) Eco-safe aspect of AgNPs: Ag nano particles are used in treating burn wounds in the form of ointments and bandages. Several commercial products are being used Immobilized AgNPs are used in urinary catheters to avoid nosocomial infections in urinary tract infections. In addition to these well established antibacterial applications, AgNPs are reported to have virucidal activity as well.

3) Free from toxic antimicrobials: The 'instant' and 'persistent' hand sanitizing hydrogel compositions of the present invention are environmentally safe since all ingredients are renewable and biodegradable. The compositions are free from halogenated as well as quaternary ammonium type of antimicrobials which are toxic to the environment as well as have leave-on' effect on human skin. The present invention uses fatty acids of Tung seed oil in hydro-alcoholic gels for the persistent sanitization using complex of silver nanoparticles and fatty acids of Tung seed oil. The fatty acids of Tung oil possess antimicrobial activity against both Gram positive and Gram negative bacteria, yeast and mold. Use of anti-microbial fatty acids of Tung seed oil derived from the triglyceride oil of seeds of the nuts, obviates the use of all synthetic antimicrobials that are synthesized using hazardous chemicals, that are reported to have serious toxicity issues ranging from allergy to neurotoxicity to carcinogenicity in humans and in some cases toxic to other form of life in the environment. Examples of such synthetic antimicrobials chlorinated (in general halogenated) molecule like chlorhexidine gluconate, Triclosan, p-chlorometaxylenol, iodopropynyl butyl carbamate or quaternary ammonium compounds like benzalkonium chloride or formaldedyhe releasing urea derivatives like diazolidinyl urea and DMDM hydantoin. Human can't leave these toxic chemical on the skin for a long time to get the 'persistent' protection via hydro-alcoholic gel composition.

4) Prevents drying of skin by reduced frequency of application of hydro-alcoholic sanitizer: Use of fatty acids of Tung seed oil not only offers 'persistent' antimicrobial protection but it reduces the frequency of usage and thereby reduces the load on the environment and prevents excessive drying of hands due to ethyl alcohol content of these gels. The reduced frequency of usage of alcohol containing sanitizer on hands prevents extreme drying of skin due to stripping off natural lipids of uppermost layer of skin, the stratum corneum.
5) Uses ingredients from renewable sources: The compositions of the present invention, unlike prior art, are made from 'renewable' materials with 'natural origin index' of minimum 99.0% as per the definition of ISO 16128-2.
6) Eco-safe aspect and useful properties of fatty acids of Tung seed oil: Fatty acids of Tung seed oil comprises of α-Eleostearic acid, linolenic acid, palmitic acid and oleic acid. The last three acids occur in many other edible vegetable oils and are completely safe. The predominant α-Eleostearic acid (ESA) of Tung seed oil also occurs in the seed of Bitter Gourd. ESA is reported to possess anti-inflammatory property. It has been shown to ameliorate inflammatory bowel disease in animals via dietary route. Korean scientists reported ESA in cure of breast cancer.
7) Immobilized silver nanoparticles, Enhanced safety measure: Immobilization of AgNPs by fatty acids of Tung seed oil reduces the possibility of toxicity stemming from nanoparticles significantly. The present invention exploits drying property of fatty acids derived from Tung seed oil for temporarily immobilizing the AgNPs on the hand surface. The drying polyunsaturated fatty acid such as α-eleostearic acid forms film by reacting with atmospheric oxygen and creates ether linkage between the long alkyl chains. The immobilizing of AgNPs in this manner makes the use of nano particles safe from any possibility of absorption through skin.
8) Stabilization of AgNPs and immobilization via π-complex formation: The unsaturated fatty acids present in the compositions of the present invention stabilize AgNPs by forming complexes. The 'persistent' sanitizer compositions of the present invention do not show any aggregation of silver nano particles on standing due to π-complex formation between metal particles and the polyunsaturated fatty acid, particularly, α-eleostearic acid. The π-complex between the metal and unsaturated sites of fatty acids also prevents metal's oxidation to ionic silver ($Ag^+$) and thereby avoiding the unwanted reactions due to hyperactivity of silver ion.

EXAMPLES

The details of the invention provided in the following examples are given by the way of illustration only and should not be construed to limit the scope of the present invention.

Lauryl polyglucoside used for AgNPs synthesis is procured from LG Care, South Korea and the trade name is Elotant Milcoside 200. Tung oil is procured from Arista Industries, USA.

Example 1: Synthesis of Silver Nanoparticles Using Lauryl Polyglucoside (APG)

To a stirred solution of lauryl polyglucoside (35.0 g, 48.88 mmol, in 900 mL water at 90° C.) under nitrogen, was added silver nitrate solution (8.5 g in 100 mL water, 50.0 mmol) in twenty parts over 2 h while continuously monitoring and maintaining the pH at 8.5 to 9.0 using NaOH solution. The color of the solution gradually turned to dark yellow. The resultant one liter of nanoparticle colloid had silver content equivalent to 5400 ppm of Ag. This was subsequently diluted to a colloid with 2000 ppm concentration.

It displayed characteristic surface plasmon resonance at 413 nm.

Particle size and zeta potential were analyzed on 90 Plus Particle size analyzer from Brookhaven Instruments Corporation: particle size was found to be 55 nm and zeta potential was found to be −24 mV.

Transmission Electron Microscopy was performed on HR-TEM 200 Kv (Jeol model JEM2100F) and particle size was found to be around 15 nm and shape to be spherical (FIGS. 7A and 7B).

Example 2: Synthesis of Fatty Acids from Tung Seed Oil

A mixture of Tung seed oil (50 g, 0.056 gmol), sodium hydroxide (48% solution, 16 g, 0.2 gmol) in ethanol (220 mL) was stirred under reflux (75° C.) for 4 h. The reaction mass was concentrated by recovering ethyl alcohol by distillation (140 mL). To the residual mass, water (100 mL) was added and stirred for half an hour at 75° C. It was then poured into water (1 liter) and the whole mixture was acidified (pH 2.0) with concentrated hydrochloric acid to precipitate the fatty acid. The whole mass was heated to 75° C. to keep the liberated fatty acid in the molten condition for the ease of subsequent phase separation and washing with water to afford fatty acid (41.0 g) as pale yellow colored liquid that solidified slowly.

The analysis of fatty acids derived from Tung seed oil is as follows: The off-white solid with melting range of 41 to 48° C. Moisture content: 0.2%, Acid value: 207 mg KOH/g, Iodine value 164 mg of Iodine per gram of sample.

UV: λmax 270 nm, E1% 1 cm: 1604, IR: 1707 cm$^{-1}$ carbonyl of carboxyl group and sharp 995 cm$^{-1}$ (FIG. 8)

Figure 9:
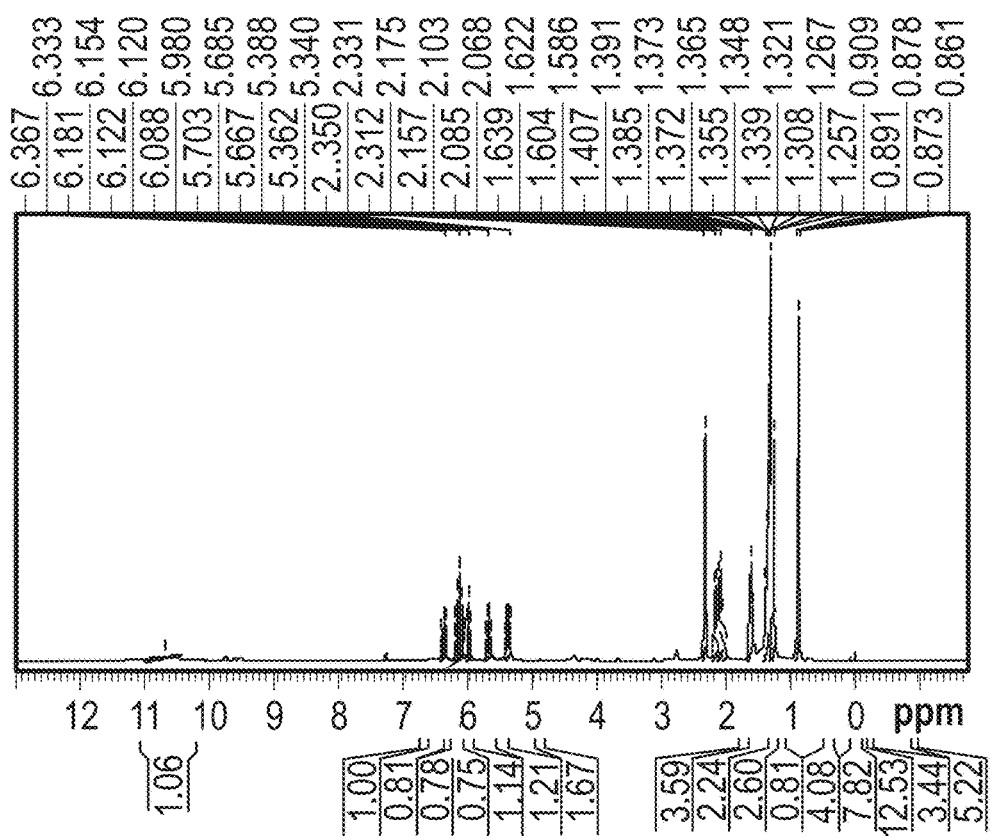
FIG. 9: Depicts the NMR spectrum of fatty acids derived from Tung seed oil.

$^1$H NMR (CDCl$_3$, 400 MHz): δ$_H$ 0.861-0.909 (m, —CH$_3$), 1.257-1.411 (m, —CH$_2$—), 1.586-1.639 (m, —CH$_2$—), 2.002-2.191 (m, —CH═CH—CH$_2$—), 2.331 (t, J=7.60 Hz, —CO—CH$_2$—), 5.362-5.407 (m, —CH═CH—, cis), 5.685 (dt, J=14.4 Hz and 7.2 Hz, —CH═CH—, cis), 5.980 (t, J=11.2 Hz, —CH═CH—, trans), 6.059-6.181 (m, —CH═CH—, trans), 6.365 (td, J=11.2 and 2.0 Hz, —H═CH—, trans), 10.685 (s, —COOH) (FIG. 9)

TABLE 3

| | |
|---|---|
| UV detection at | 270 nm |
| Flow rate | 1 mL/min |
| Injection volume | 100 μL |
| Temperature | 40° C. |
| Column | Agilent TC C18 (250 × 4.6 mm); 5 μm or any equivalent C18 column |
| Run time | 55 min |
| Mobile phase | Gradient (water containing 0.1% phosphoric acid and acetonitrile |

The fatty acids derived from Tung seed oil are resolved by 'reversed phase' chromatography using water-acetonitrile gradient solvent system starting from 1:1 to 100% acetonitrile. The analysis of hydrolyzed commercial Tung seed oil does show ESA (α-Eleostearic acid) to be around 82%. The other C18 acids have been, oleic and linoleic, around 6% each. The saturated fatty acids are found to be 2 to 4% (Table 4).

TABLE 4

| Retention Time | Area % | Name |
|---|---|---|
| 33.840 | 0.30 | Lauric Acid |
| 38.807 | 81.38 | α-Eleostearic acid |
| 40.060 | 6.89 | Linoleic acid |
| 40.493 | 0.28 | Myristic acid |
| 42.773 | 6.14 | Oleic acid |
| 43.327 | 2.34 | Palmitic acid |
| 50.893 | 2.67 | Stearic acid |

Example 3: General Procedure for Preparation of Hydro-Alcoholic Gels Using Vegetable Derived Gelling Agents Vegetable carbohydrate based (0.2 to 2.0%) gelling agent/thickener was soaked in water for several hours. To it, ethyl alcohol was added under stirring at room temperature. The pH of the whole mix was adjusted to 6.5 to 7.5 using sodium hydroxide or citric acid. Rest of the ingredients (stock solution of AgNPs as per Example 1, skin benefit agent of natural origin, fatty acids of Tung seed oils derived as per Example 2), were added in any sequence.

TABLE 5

| | Components | | | | | | | | |
|---|---|---|---|---|---|---|---|---|---|
| | Comp. I | Comp. II | Comp. III | Comp. IV | Comp. V | Comp. VI | Comp. VII | Comp. VIII | Comp. IX |
| Ethyl alcohol | 70 | 70 | 70 | 70 | 70 | 70 | 70 | 65 | 65 |
| Hydroxy propyl cellulose | 1.5 | 1.5 | 1.5 | | 1.5 | 1.0 | 1 | | 1 |
| Sodium hyaluronate | | | | | | | | | 1.0 |
| Hydroxy ethyl cellulose | | | | | | | | 2.0 | |
| AgNPs | 10 ppm | 10 ppm | 25 ppm | 10 ppm | 10 ppm | | | 25 ppm | 25 ppm |
| Fatty acids of Tung seed oil | | 1 | 1 | 2.0 | 3.0 | 3.0 | | 2.0 | 2.0 |
| Glycerin | | | | | | | | 3 | 3 |
| Tea tree oil | | | | | | | | 0.2 | 0.2 |
| Aloe Vera leaf extract | | | | | | | | 0.2 | 0.2 |
| Soya protein hydrolyzate | | | | | | | | 0.2 | 0.2 |
| Water | To make 100 | To make 100 | To make 100 | To make 100 | To make 100 | To make 100 | To make 100 | To make 100 | To make 100 |
| Viscosity | <1000 Cps | <1000 Cps | <1000 cps | <1000 Cps | <1000 cps | <1000 Cps | <1000 Cps | <1000 cps | <1000 Cps |
| Microbial growth (4 hours) Finger impression method | <20 CFU | <10 CFU | 2 CFU | 2 CFU | No colony | <20 CFU | TNTC | <10 CFU | <10 CFU |

Viscosities of hydroalcoholic gels ranging from 200 cps to 2500 cps were obtained by varying the amount of gelling agent, amount of water and the type of gelling agent and its average molecular weight.

Example 4: Preparation of Hydroalcoholic Solution of AgNPs (100 ppm) and Fatty Acid of Tung Seed Oil Using stock solution of Example 1, a hydro-alcoholic solution (70% ethyl alcohol and 30% water) with 100 ppm concentration of AgNPs and 3% of fatty acids of Tung seed oil (derived from Example 2) was prepared. The hydro-alcoholic solution obtained is a clear, deep yellow colored solution with pH of 6.5.

Figure 11:
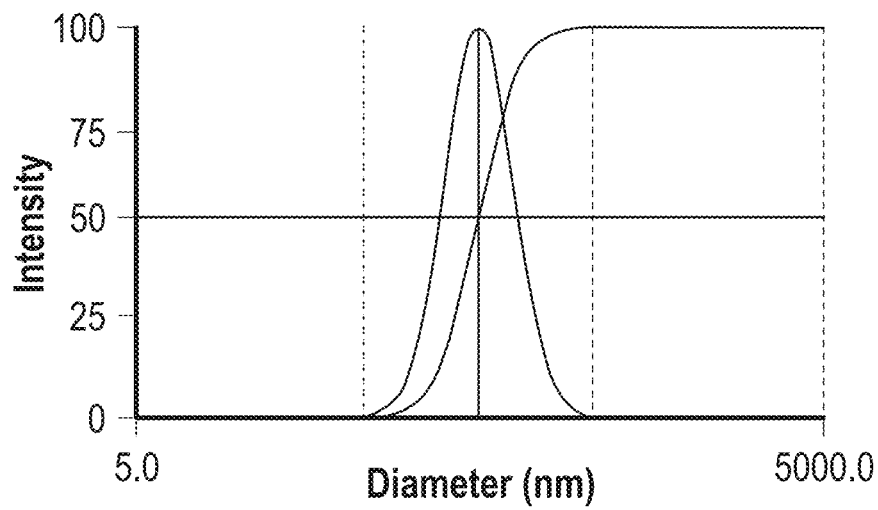
FIG. 11: Depicts Dynamic light scattering analysis (using 90 Plus Particle size analyzer, Brookhaven Instruments Corporation) of hydroalcoholic solution of Example 4.
Figure 12:
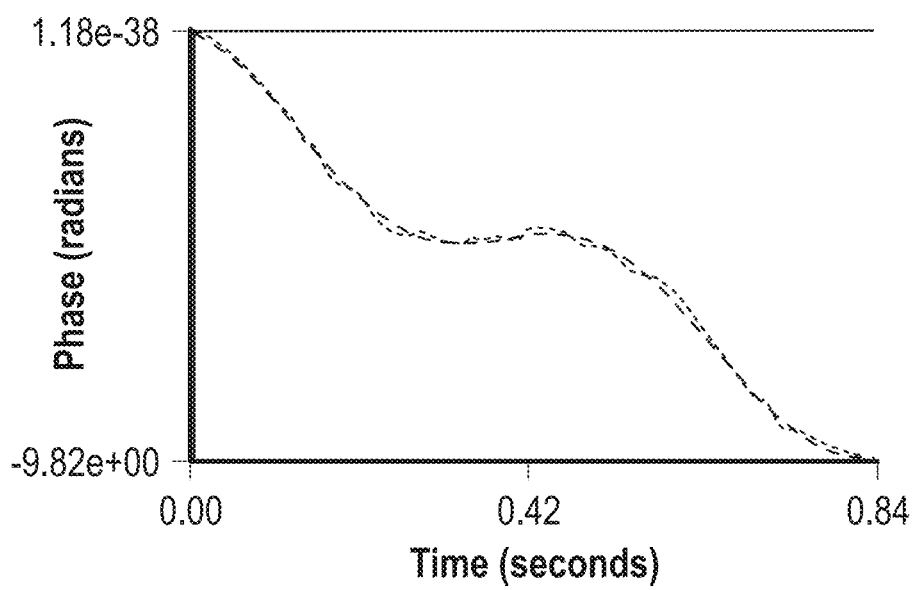
FIG. 12: Depicts zeta potential of Silver nanoparticles solution of Example 4.

This was further diluted to 5 ppm concentration with a mixture of ethyl alcohol and water (70:30). Dynamic light scattering analysis (90 Plus Particle size analyzer, Brookhaven Instruments Corporation) showed the particle size to be 158 nm (FIG. 11) and Zeta potential was found to be −24 mV (FIG. 12).

Example 5: Evaluation of Anti-Microbial Efficacy (Persistent Effect) of Hand Sanitizer Formulation by Finger Impression Method Fixed quantity of hydro-alcoholic gel of (Table 5, Compositions I to IX) was applied to hands the way sanitizing gels are applied. The gel was spread uniformly by rubbing the palms of the hand against each other. After four hours, the finger impressions were taken to check if the remnant content left on the hands after alcohol was evaporated, protects the palm's surface from getting re-contaminated. This technique of visual observation of bacterial growth from handprints (handprint culture before application of alcohol based sanitizer and handprint culture after alcohol based sanitizer was applied) was adopted from literature protocol that was predominantly used to improve hand hygiene of health workers. [a] WHO guidelines on hand hygiene in health care, 2009; b) Alebaly et al. (2018) Influence of Handprint Culture Training on Compliance of Healthcare Workers with Hand Hygiene, Hindawi Interdisciplinary Perspectives on Infectious Diseases, Volume, Article ID 3727521, (https://doi.org/10.1155/2018/3727521); c) Ewoud Reilman, Joke G. Hagting et al. (2015) Towards an antimicrobial 'micro-glove' Scientific Reports, 5:16679, DOI: 10.1038/srep16679 (https://www.nature.com/articles/srep16679); d) Y. Yamamoto et al. in 'Usefulness of training in hand hygiene using full hand touch method for hospital staff'; *Japanese Journal of Infection Prevention and control*, vol. 30, no 4, pp 281-287, 2015].

Finger impression before application of sanitizer gel: Finger impressions were taken on the pre-prepared Nutrient Agar medium plates containing 1% Tetrazolium chloride (2,3,5-triphenyl-2H-tetrazolium chloride). The plates were opened in aseptic conditions (laminar flow unit) to prevent accidental contamination. Finger impressions were taken for about 10 seconds and plates were covered with the lids and incubated.

Finger impression immediately (Zero hour) after the application of sanitizer gel: Hand sanitizer gel (2.0 g, Compositions I to IX, Table 5) was then applied uniformly by hand rub method. Alcohol evaporates in few seconds and immediately finger impression was taken as described above. On incubation for 72 hours aerobically at 35° C., colony count was found to be zero, occasionally, one. Instant sanitization of hands seems effective due to 65 to 70% alcohol content of gel compositions.

Finger impression four hours after the application of sanitizer gel: Hand sanitizer gels (2.0 g, compositions I to IX, Table 5) were then applied uniformly by hand rub method. Alcohol evaporates in few seconds and normal activity is resumed. The finger impression was taken after performing the normal office work or lab work for four hours by following the same protocol of opening the Agar nutrient plates in laminar flow unit. The covered plates were then incubated aerobically at 35° C. for 72 hours.

The FIG. 4 of the petri-plates illustrated the study of composition V. The first plate in FIG. 4 showed the impression of fingers before applying the sanitizing gel.

Microbial colonies were too numerous to count. Redox indicator Tetrazolium chloride dye (TTC) helped with the visual observation. The second petri-plate showed microbial colonies that represented the status of fingers immediately after the application of sanitizer gel of composition V and showed no bacterial colonies after incubation. Third plate showed the bacterial colony count after four hours of application of sanitizing gel. During this period of four hours normal activity with hands was performed. It can be seen that in the third petri-plate, formation of bacterial colonies was not at all observed.

Example 6: Water-Repellant Film Formation and Immobilization of AgNPs

Hydro-alcoholic gels of composition I and V (Table 5) were spread on the internal surface of big petri-plate. It was allowed to dry at 37° C. (human body temperature) for two hours. Water (10 mL) was added on the film and gently swirled. The water was removed carefully by a pipette in a 10 mL volumetric flask. The volumes were made up to mark. Silver content of both water extract of composition I and V were analyzed by inductively coupled plasma—optical emission spectroscopy (ICP-OES) analysis.

The aqueous extract of composition I showed almost 90% recovery of Ag whereas aqueous extract of composition V showed that the recovered Ag was only 10% and 90% of Ag was retained by the film in the petri-plate.

From the above it was demonstrated that, a hydro-alcoholic gel composition of present invention containing fatty acids derived from Tung seed oil, effectively immobilize AgNPs and therefore prolong the 'sanitized' state of the surfaces.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

We claim:

1. A safe and ecofriendly sanitizing hydro-alcoholic gel composition for topical application with instant and persistent antimicrobial activity comprising:
   a) 60 to 70% by weight of ethyl alcohol;
   b) 5 to 100 ppm by weight of silver nanoparticles;
   c) 0.2 to 5% by weight of fatty acids derived from Tung seed oil, wherein at least about 80% of the fatty acids are α-eleostearic acid (ESA);
   d) 0.2 to 2% by weight of carbohydrate based gelling agents/thickeners;
   e) optionally, 1 to 5% by weight of skin benefiting agents; and
   f) demineralized water to make up 100% w/w, wherein at least a portion of the silver nanoparticles and at least a portion of the ESA are present in the form of ESA-silver nanoparticle complexes where the ESA acts as a ligand and prevents aggregation of the silver nanoparticles in the hydro-alcoholic gel composition, and wherein the α-eleostearic acid-silver nanoparticle complexes exhibit a surface plasmon resonance UV absorbance at 460 nm.

2. The sanitizing hydro-alcoholic gel composition as claimed in claim 1, wherein the fatty acids derived from Tung seed oil stabilize and immobilize the silver nanoparticles in the composition and thus provides a water repellent film and an antimicrobial shield for a prolong period after evaporation of the alcohol.

3. The sanitizing hydro-alcoholic gel composition as claimed in claim 1, wherein the carbohydrate based gelling agents/thickeners are selected from hydroxyl ethyl cellulose, hydroxyl propyl cellulose and sodium hyaluronate.

4. The sanitizing hydro-alcoholic gel composition as claimed in claim 1, wherein the composition comprises the skin benefiting agents.

5. The sanitizing hydro-alcoholic gel composition as claimed in claim 4, wherein the skin benefiting agents are selected from soya protein hydrolyzate, glycerin, tea tree oil and *Aloe vera* leaf juice.

6. The sanitizing hydro-alcoholic gel composition as claimed in claim 1, wherein the composition comprises 5 to 25 ppm by weight of the silver nanoparticles.

7. The sanitizing hydro-alcoholic gel composition as claimed in claim 1, wherein the composition comprises 10 to 25 ppm by weight of the silver nanoparticles and 1 to 3% by weight of the fatty acids derived from Tung seed oil.

8. A process for preparing a sanitizing hydro-alcoholic gel composition according to claim 1, comprising:

a) soaking a carbohydrate based gelling agent/thickener in demineralized water followed by adding ethyl alcohol to form a mixture;

b) adjusting the pH of the mixture to 6.5-7.5;

c) adding a stock solution to the mixture, the stock solution having demineralized water, silver nanoparticles, fatty acids derived from Tung seed oil where at least about 80% of the fatty acids are α-eleostearic acid (ESA), and optionally skin benefitting agents and stirring to obtain the hydro-alcoholic gel composition, wherein at least a portion of the silver nanoparticles and at least a portion of the ESA react to form ESA-silver nanoparticle complexes.

9. The process as claimed in claim 8, wherein the hydro-alcoholic gel composition has a viscosity ranging from 200 cps to 2000 cps.

10. The process as claimed in claim 8, wherein the pH of the mixture is adjusted using sodium hydroxide or citric acid.

* * * * *